(12) United States Patent
Nordin et al.

(10) Patent No.: US 6,414,312 B1
(45) Date of Patent: *Jul. 2, 2002

(54) METHOD FOR CONTROLLING A PROCESS FOR THE PRODUCTION OF A CELLULOSE FIBER CONTAINING PRODUCT

(75) Inventors: Sofia Nordin; Bo Johnsson; Björn Engström, all of Sundsvall (SE)

(73) Assignee: Akzo Nobel N.V., Arnhem (NL)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/263,103

(22) Filed: Mar. 5, 1999

Related U.S. Application Data

(60) Provisional application No. 60/076,927, filed on Mar. 5, 1998.

(30) Foreign Application Priority Data

Mar. 5, 1998 (EP) ............................................ 98850031

(51) Int. Cl.⁷ .............................................. G01N 21/17
(52) U.S. Cl. ............................ 250/339.09; 250/339.08; 250/339.11
(58) Field of Search ........................ 250/339.07, 339.08, 250/339.09, 339.1, 339.11, 339.12, 338.5, 339.01, 339.02, 341.8

(56) References Cited

U.S. PATENT DOCUMENTS

| | | | |
|---|---|---|---|
| 4,609,628 A | * | 9/1986 | Aschenbeck ................. 436/34 |
| 5,532,487 A | | 7/1996 | Brearley et al. |
| 5,942,058 A | * | 8/1999 | Sleeter et al. .............. 156/62.2 |

FOREIGN PATENT DOCUMENTS

| | | |
|---|---|---|
| EP | 0 564 013 | 10/1993 |
| WO | WO 97/04299 | 2/1997 |

OTHER PUBLICATIONS

I. Murray and P. C. Williams, "Chemical Principles of Near–Infrared Technology", *Near–Infrared Technology in the Agricultural and Food Industries*, Edited by Phil Williams and Karl Norris, AACC, St. Paul Minnesota, pp. 17–31 (1987).

Carlson, "Design and optimization in organic synthesis", *Data Handling in Science and Technology*, vol. 8, pp 451–488 (1992).

Geladi et al, "Partial Least–Squares Regression: A Tutorial", *Analytica Chimica Acta*, 185, pp 1–17 (1986).

Brown, "Chemomtrics", *Analytical Chemistry*, vol. 62, No. 12, pp 84R–101R (1990).

Maloney, *Modern Particleboard & Dry–Process Fiberboard Manufacturing*, pp 25–29 and 626–634 (1993).

Kubelka et al, *Physik* 12, 593–601 (1931).

Geladi et al, "Linearization and Scatter–Correction for Near–Infrared Reflectance Spectra of Meat", *Applied Spectroscopy*, vol. 39, No. 3, pp 491–500 (1985).

Savitzky et al, "Smoothing and Differentiation of Data by Simplified Least Squares Procedures", *Analytical Chemistry*, vol. 36, No. 8, pp 1627–1639 1964.

O'Havar et al, "Signal–to–Noise Ratio in Higher Order Derivative Spectrometry", *Analytical Chemistry*, vol. 53, No. 12, pp 1876–1878 (1981).

Barnes et al, "Standard Normal Variate Transformation and De–trending of Near–Infrared Diffuse Reflectance Spectra", *Applied Spectroscopy*, vol. 53, No. 5, pp 772–777 (1989).

Stark et al, "Near–Infrared Analysis (NIRA): A Technology for Quantitative and Qualitatie Analysis", *Applied Spectroscopy Reviews*, 22:4, pp 335–399 (1986).

* cited by examiner

*Primary Examiner*—Constantine Hannaher
*Assistant Examiner*—Albert Gagliardi
(74) *Attorney, Agent, or Firm*—Burns, Doane, Swecker & Mathis, L.L.P.

(57) ABSTRACT

A method for controlling a process for the production of a cellulose fiber containing product, during which at least two substances having a substantial influence on the same property of said product in correspondence to the relation between them are added, whereby a calibration model has been established by linking reference property values and corresponding reference relations, by means of a mathematical function, and in that the method comprises applying the calibration model on the actual relation in order to predict the property value; comparing the predicted property value with a desired target property value; and, if said predicted value is not substantially equal to said target value, adjusting the actual relation in a predetermined way; and repeating these operations until said predicted value is substantially equal to said target value.

18 Claims, No Drawings

METHOD FOR CONTROLLING A PROCESS FOR THE PRODUCTION OF A CELLULOSE FIBER CONTAINING PRODUCT

This application claims priority under 35 U.S.C. §§119 to U.S. Provisional Application No. 60/076,927 filed Mar. 5, 1998.

FIELD OF THE INVENTION

The present invention relates to a method for controlling a process for the production of a cellulose fibre containing product from cellulose fibre containing raw material, in particular a process for the production of wood based panels such as particleboards.

DESCRIPTION OF THE RELATED ART

The production of cellulose fibre containing products often involve addition of different substances during the production process. The purpose of the addition may be to facilitate the production process per se, or to effect the resulting product, or both. Addition of various glues, often consisting of a glue system comprising a resin and a hardener, in the production of wood based panels is exemplary of an addition in order to effect the resulting product. An important parameter in this connection is often the proportion between the components making up the substance, if more than one, such as e.g. the proportions between resin and hardener in a glue, or the proportions between urea and formaldehyde in a glue containing those components. Another important parameter may be the proportions between different added substances, which are destined to different parts of the panel, e.g. in different layers of the panel.

WO 97/04299 relates to a method for controlling process variables influencing parameters of wood based panels, including glue amounts and wax amounts, which method comprises analysing the raw material by means of a spectrometric method, linking the obtained spectral data into a combination with desired parameters, and comparing said combination with reference combinations consisting of reference data from reference raw material linked with known parameters of said reference material, whereby the reference combinations have been calibrated to known variables by means of multivariate analysis. There is however no suggestion about controlling any proportions relating to those additives.

It would however be desirable to be able to control such proportions, as by doing so, it should be possible to produce cellulose fibre containing product such as wood based panels with very specific properties at optimised technical and economical conditions.

BRIEF SUMMARY OF THE INVENTION

The problem to be solved by the present invention is thus to enable such controlling.

This problem has been solved by the invention as defined by the appended claims. More particularly the present invention involves a method for controlling a process for the production of a cellulose fibre containing product from cellulose fibre containing raw material, during which process various substances are added, at least two of which substantially influence the same property of said product in correspondence to the relation between said substances, whereby a calibration model has been established by way of a procedure comprising linking known reference values for said product property and corresponding known reference relations between the substances, by means of a mathematical function; the method comprises the steps of I) applying the calibration model on the actual relation between the substances in order to predict the value for said product property;
II) comparing the predicted value for said product property with a desired target value for said product property;
and, if said predicted value is not substantially equal to said target value, adjusting the actual relation between the substances in a predetermined way;
III) repeating steps I and II until said predicted value is substantially equal to said target value.

By the expression "in a predetermined way" is, in the present context, partly meant that it has been determined in advance whether the relation should be adjusted at all in the present turn in the loop defined by steps I to III; partly meant that it has been determined in advance whether the adjustment should be incremental or decremental depending on the fact per se that the predicted value is larger that the target value, irrespective of the size of the difference between those values, and vice versa, and partly meant that the absolute value of the adjustment has been determined in advance.

DETAILED DESCRIPTION OF THE INVENTION

The present method presents a plurality of advantages to the producer of cellulose fibre containing products. By means of the present method a particleboard producer, for instance, can regulate one or more properties of the produced boards in a very fast and economical way.

In a preferred embodiment the calibration model has been established by means of a multivariate analysis; this also implies that the same kind of multivariate analysis is applied when the calibration model is applied on the actual relation. The multivariate analysis may, for instance, be principal component analysis (PCA), partial least squares regression (PLS), principal component regression (PCR), multilinear regression analysis (MLR), discriminant analysis, or any other suitable method for multivariate analysis. The PLS method is disclosed in detail in Carlson R., "Design and optimization in organic synthesis", B. G. M. Vandeginste, O. M. Kvalheim, Eds., "Data handling in science and technology", (Elsevier, 1992), vol. 8, incorporated herein by reference. For a tutorial in PCA, PLS and PCR, see P. Geladi et al in "Partial Least-Squares Regression: A Tutorial" in Anal. Chim. Acta, 185, 1–17 (1986), which is incorporated herein by reference in its entirety. By MLR, the best fitting plane for the parameters as a function of the spectra is defined, using least squares techniques to define each boundary of the plane. This plane is then used to recognize and assign a predicted value to an unknown parameter value. Discriminant Analysis is a method whereby, by use of spectral data, the known parameter values are grouped into different clusters, separated by linear decision boundaries. From its spectrum, a sample of unknown parameter values then can be matched to a cluster, and the parameter value can be assigned a value, e.g., the average value of the cluster. Applied generally to the field of chemistry those statistic methods are also termed chemometrics methods. The technique of chemometrics is more fully explained in S. D. Brown, "Chemometrics", Anal. Chem. 62, 84R–101R (1990), which by reference is incorporated herein in its entirety.

In a preferred embodiment the cellulose fibre containing product is a wood based panel. The wood based panel may comprise two or more layers. One of the substances may for instance be added to substantially stay between the layers, in order to e.g. agglutinate (i.e. glue together) the layers. Alternatively, one substance may be added to be substantially contained within one of the layers, in order to e.g. bind wood based particles in a particle board, or to provide the layer with some property, or to enhance some already present property. The wood based panel is preferably a board, such as a particleboard, a medium density fibre board (MDF), a waferboard, an oriented strand board (OSB), a hardboard, or a board of plywood; in particular, the board is a particleboard. Background information on particleboard and the processes for the manufacturing thereof is set forth in "Modern Particleboard & dry-process fibreboard manufacturing" by Thomas M. Maloney (1993), (cf. especially Chapter 4 and 5), which by reference is incorporated herein in its entirety.

It should be understood that the two (or more) substances which have a substantial influence on the same property of said product in correspondence to the relation between said substances may very well lack any effect, or only have a weak effect on that (or any other) property when used isolated from each other. This, basically, is the case when, for instance, one substance is a resin and another one is a corresponding hardener. On the other hand, the effect of the substances may in another embodiment be of basically the same magnitude, e.g. when using two urea-formaldehyde glues having different U/F proportions. In the latter case the property of interest can be brought towards its target value by controlling the U/F proportion of an actually added, mixed glue within a range defined by the U/F proportions of the two glues, by applying the present method on the relation between the added and mixed amounts of the glues. If instead the glues are added to different layers of a board, and thus basically are not mixed with each other, the property of interest can still be controlled, and in this case the actual relation between the added, but not mixed, substances is used in the construction and application of the calibration model.

In one embodiment each one of the substances is a glue containing an amino resin, such as for instance a urea-formaldehyde resin (UF), a melamine-urea-formaldehyde resin (MUF), or a phenol-formaldehyde resin (PF), whereby the substances may differ from each other with regard to e.g. the content of formaldehyde. Other glues may however also be used, such as e.g. isocyanate resin (MDI).

The product properties that can be controlled by the present method are for instance density, density profile, internal bond strength, thickness swelling, absorption value, permeability value, perforator value, modulus of rapture (MOR), modulus of elasticity (MOE), parameters relating to volatile organic compounds (VOC), and emission chamber value; this, however, is not an exhaustive list of controllable properties. Basically any measurable property of the product may be controlled by the present method.

The total amount of substance is often also important with regard to the resulting product property. Thus, in one embodiment of the invention, in which the two substances have a substantial influence on said property also in correspondence to the added combined amount of the substances, the calibration model involves linking said known values for said product property with the corresponding known combined amounts of the substances added and the corresponding relations between the substances in said amounts; and the application of the calibration model involves linking of the actual relations between the substances and the corresponding relations between the substances in said amounts in order to predict the actual value for said product property.

In a particularly preferred embodiment of the present method the calibration model has been established by way of a procedure comprising analysing reference raw material, by means of an analysis method, to provide reference sample data, and linking said reference sample data with known values for said product property and corresponding known relations between the substances, by means of said mathematical function; the method additionally comprises the step of analysing the raw material, by means of said analysis method, to provide sample data; and the application of the calibration model involves linking of the sample data with the relation between the substances in order to predict the actual value for said product property.

This embodiment provides additional advantages to the producer of cellulose fibre containing products. By means of the present method a particleboard producer, for instance, may manufacture boards with high surface strength even from wooden raw material of inferior quality by compensating the lacking quality with a urea-formaldehyde glue having a high molar proportion of formaldehyde, which is used in the surface layer of the board, while the control of the dosage and the molar proportion of formaldehyde in the glue in the core layer based upon other desired properties such as for instance a specified density and/or a low formaldehyde emission value.

The sample data is preferably transferred into latent variables before being linked with the target value, as are preferably the reference sample data before they are linked with said known values.

In a particularly preferred embodiment of the present invention the analysis method is a spectrometric method. The sample data as well as the references sample data is preferably processed in this instance to reduce noise and is also suitably adjusted for drift and diffuse light scatter, for instance by means of the Kubelka-Munk transformation (P. Kubelka, F. Munk, Z. Tech. Physik 12, 593 (1931), incorporated herein by reference), which takes account of absorption and scatter, the Multiplicative Scatter Correction (P. Geladi, D. MacDougall, H. Martens, Appl. Spect. 39, 491–500 (1985), incorporated herein by reference) where each spectrum is "corrected" in both offset and slope by comparing it to an "ideal" spectrum (the mean spectrum). Another way of linearizing the spectral data involves the use of derivatives, e.g. up to the fourth order derivatives (A. Savitzky, M. J. E. Golay, Anal. Chem. 36, 1627–1639 (1964), incorporated herein by reference). The derivative of the spectrum results in a transformed spectrum, consisting only of the relative changes between the adjacent wavelengths, and it has been shown that the peak intensities of derived spectra tend to be more linear with concentration (T. C. O'Haver, T. Begley, Anal. Chem. 53, 1876 (1981), incorporated herein by reference). Linearization can also be accomplished by use of the Fourier transformation, or by use of the Standard Normal Variate transformation (R. J. Barnes, M. S. Dhanoa and S. J Lister, Appl. Spectrosc., Vol. 43, number 5, pp. 772–777 (1989), incorporated herein by reference). This noise reduction/drift and diffuse light scatter-adjustment is suitably done before the data is linked as set forth above. The spectrometric method may be an absorption, reflectance, emission or transmission spectrometric method, or any other conceivable spectrometric method. Although the spectrometric method may relate to any suitable kind of radiation at any wavelength range, it is preferred to use a spectrometric method operating in the wavelength range from about 180 to about 2500 nm, particularly from about 400 to 2500 nm, and especially from about 1000 nm to about 2500 nm. It is particularly preferred to operate the present method in the near-infrared radiation (NIR) range. The principles of NIR spectroscopy are described by Williams, P.; Norris, K. (1987): Near-Infrared Technology in the Agriculture and Food Industries, AACC, St. Paul/Min. and Stark, E.; Luchter, K. (1986): Near Infrared Analyses (NIRA) A Technology for Quantitative and Qualitative Analyses. (Applied Spectroscopy Revues 22:4), all of which are hereby incorporated by reference.

Technically, the spectrometric analysis can be performed by on-line, in-line or at-line optical fibre probing, or by taking individual samples for separate analysis. In any case the spectra are preferably subjected to further data treatment using values from several discrete wavelengths from each particular spectrum. The radiation used in the spectrometric method preferably impinges directly on the raw material.

In a specifically preferred embodiment of the present invention the produced cellulose fibre containing product is a particleboard comprising one core layer and two surface layers; the cellulose fibre contains raw material comprises sawdust, shavings, chips or shavings from round wood, or a combination thereof; the controlled product property is density, density profile, internal bond strength, MOR, MOE, thickness swelling, absorption value, permeability value, perforator value, or emission chamber value; the substances are glues obtained by mixing formaldehyde, urea, and optionally any other suitable component; and the glues differ from each other with regard to the proportions between formaldehyde and urea, whereby a first glue holds a higher proportion between formaldehyde and urea than a second glue.

In another embodiment the present method for controlling a process for the production of a cellulose fibre containing product is combined with EP 564,013, which relates to a method and a device for mixing binders using at least two components which are flowed from separate storage containers towards a common mixing point. The storage containers are continuously weighed, and their change of weight per unit of time is determined.

The present invention will now be further illustrated by means of some non-limiting examples.

EXAMPLES

Particleboards having a core layer and two surface layers were produced by mixing core and surface particles with urea-formaldehyde resin glue, forming the mixtures into 330×500 mm sheets, and pressing the sheets for 2.7 minutes at 185° C. Two slightly different urea-formaldehyde resin glues were used, both based on the same kind of urea-formaldehyde resin, Cascorit UF 1110 from Casco Products, Industrial Resins Division, Sundsvall, Sweden. One glue, glue A, had a formaldehyde to urea ratio, F/U ratio, of 0.9 and the other glue, glue B, had a F/U ratio of 1.3. Both glues contained 0.4 wt-% of wax (Kenosize 4550 from Casco Products, Sweden). The viscosities of the glues were about 300 mPas for glue A and about 800 mPas for glue B.

Following a $2^4$ experiment design having two centre points, a series of 18 particleboards were produced. Glue A and B were added to the core and the surface layers in varying amounts, providing varying F/U ratios in the core and the surface layers, according to Table I below.

Ammonium sulphate was used as hardener 3.0 wt-% was added to the core layer and 1.0 wt-% to the surface layers.

TABLE 1

| board # | Total glue amount in surface layer, wt-% (YI) | Total glue amount in core layer, wt-% (MI) | F/U ratio in surface layer (Ym) | F/U ratio in core layer (Mm) |
| --- | --- | --- | --- | --- |
| 1 | 10 | 7 | 1.05 | 1.05 |
| 2 | 10 | 7 | 1.15 | 1.05 |
| 3 | 10 | 7 | 1.05 | 1.15 |
| 4 | 10 | 7 | 1.15 | 1.15 |
| 5 | 12 | 7 | 1.05 | 1.05 |
| 6 | 12 | 7 | 1.15 | 1.05 |
| 7 | 12 | 7 | 1.05 | 1.15 |
| 8 | 12 | 7 | 1.15 | 1.15 |
| 9 | 10 | 9 | 1.05 | 1.05 |
| 10 | 10 | 9 | 1.15 | 1.05 |
| 11 | 10 | 9 | 1.05 | 1.15 |
| 12 | 10 | 9 | 1.15 | 1.15 |
| 13 | 12 | 9 | 1.05 | 1.05 |
| 14 | 12 | 9 | 1.15 | 1.05 |
| 15 | 12 | 9 | 1.05 | 1.15 |
| 16 | 12 | 9 | 1.15 | 1.15 |
| 17 | 11 | 8 | 1.1 | 1.1 |
| 18 | 11 | 8 | 1.1 | 1.1 |

The boards were analysed with respect to a number of parameters:

density, determined by weighing strips of the board with known volume and dividing the mass with the volume. Values are expressed in kg/m$^3$;

internal bond (IB), which is the property of a given board to resist tension perpendicular to the plane of the board. Values are expressed in MPa;

thickness swelling (TSW), measured by placing a board sample in water of a temperature of 20 or 23° C. during 2–24 h. Thickness of the sample is measured before and after the soaking. The thickness difference is divided by the original thickness and expressed in percent;

absorption value (ABS): a sample is weighed before and after the water exposure. The weight difference is divided by the original weight and expressed in percent;

perforator value (PV), which expresses the formaldehyde content of the board at a certain moisture content (6.5%). The board is leached in toluene. The released formaldehyde is absorbed in water and determined photometrically. Values are expressed in mg HCHO/100 g oven-dry board;

Formaldehyde release by the flask method, EN 717-3 (HCHO release). Values are expressed in mg HCHO/kg oven-dry board.

The obtained parameter values are set forth in Table II below.

TABLE II

| board # | IB | TSW | PV | HCHO release |
| --- | --- | --- | --- | --- |
| 1 | 0.68 | 25.7 | 4.4 | 4.2 |
| 2 | 0.71 | 22.8 | 6.1 | 5.9 |
| 3 | 0.73 | 18.8 | 6.4 | 5.7 |
| 4 | 0.80 | 17.5 | 6.8 | 7.4 |
| 5 | 0.67 | 18.4 | 4.7 | 4.5 |
| 6 | 0.68 | 19.0 | 5.4 | 5.6 |
| 7 | 0.76 | 20.8 | 6.6 | 6.1 |
| 8 | 0.77 | 15.5 | 8.3 | 8.1 |
| 9 | 0.82 | 18.4 | 3.6 | 4.0 |
| 10 | 0.74 | 15.5 | 5.9 | 5.6 |
| 11 | 0.92 | 16.7 | 5.3 | 5.8 |
| 12 | 0.95 | 14.7 | 7.7 | 8.4 |

TABLE II-continued

| board # | IB | TSW | PV | HCHO release |
|---|---|---|---|---|
| 13 | 0.73 | 15.2 | 4.1 | 3.9 |
| 14 | 0.76 | 17.4 | 5.1 | 5.7 |
| 15 | 0.86 | 14.5 | 5.4 | 5.5 |
| 16 | 0.95 | 13.7 | 6.3 | 7.9 |
| 17 | 0.80 | 16.1 | 5.1 | 6.0 |
| 18 | 0.81 | 18.2 | 5.9 | 5.4 |

Partial least square regressions were carried out based on the values indicated above in order to find correlations between the obtained values in Table II and the parameters of Table I. The obtained coefficients of regression for these correlations are disclosed in Table III below. The coefficient of regression of an ideal correlation is 1.

TABLE III

| Parameter | Significant variables | R = coefficient of regression |
|---|---|---|
| IB | MI, Mm, Mm × MI | 0.96911 |
| TSW | MI, Mm | 0.85754 |
| PV | Mm, Ym | 0.91957 |
| HCHO release | Mm, Ym | 0.97565 |

Apparently, it is possible to predict parameter values of cellulose fibre containing products by starting out from the relation between substances added during the production. As at least a person skilled in the art will appreciate, this clearly implies that the present method can be used for controlling a process for the production of a cellulose fibre containing product from cellulose fibre containing raw material, during which process various substances are added, at least two of which have a substantial influence on the same property of said product in correspondence to the relation between said substances.

What is claimed is:

1. A control method comprising a process for the production of a wood-based panel from cellulose fiber-containing raw material, during which process various substances selected from the group consisting of glues, resins and hardeners, and mixtures thereof are added, at least two of which have a substantial influence on the same property of said wood-based panel in correspondence to the relation between said substances, wherein a calibration model has been established by way of a procedure comprising linking known reference values for the wood-based panel property and corresponding known reference relations between the substances, by means of a mathematical function, wherein the method further includes I) applying the calibration model on the actual relation between said substances selected from the group consisting of glues, resins and hardeners and mixtures thereof, said substances having a substantial influence on the same property of said wood-based panel in order to predict the value for said wood-based panel property;

II) comparing the predicted value for said wood-based panel property with a desired target value for said property; and, if said predicted value is not substantially equal to said target value, adjusting the actual relation between the substances in a predetermined way; and III) repeating steps I and II until said predicted value is substantially equal to said target value.

2. A method according to claim 1, wherein calibration model has been established by means of a multivariate analysis.

3. A method according to claim 2, wherein the multivariate analysis is selected from principal component analysis, partial least squares regression, and principal component regression.

4. A method according to claim 1, wherein the wood-based panel comprises two layers, and that one of the substances is added to substantially stay between the layers.

5. A method according to claim 4, wherein one of the substances is added to be substantially contained within one of the layers.

6. A method according to claim 4, wherein one of the substances is added to be substantially contained within one of the layers.

7. A method according to claim 1, wherein the wood-based panel is a board.

8. A method according to claim 7, wherein the board is a particle board.

9. A method according to claim 1, wherein each one of the substances is a glue containing an amino resin, whereby the substances differ from each other with regard to the content of formaldehyde.

10. A method according to claim 1, wherein said product property is internal bond strength, thickness swelling, perforator value, of formaldehyde release.

11. A method according to claim 1, wherein the two substances have a substantial influence on said property also in correspondence to the added combined amount of the substances; and the calibration model involves linking said known values for said product property with the corresponding known combined amounts of the substances added and the corresponding relations between the substances in said amounts; and in that the application of the calibration model involves linking of the actual relations between the substances and the corresponding relations between the substances in said amounts in order to predict the actual value for said product property.

12. A method according to claim 1, wherein the calibration model has been established by way of a procedure comprising analyzing reference raw material, by means of an analysis method, to provide reference sample data, and linking said reference sample data with known values for said product property and corresponding known relations between the substances, by means of said mathematical function, and in that the method additionally comprises the step of analyzing the raw material, by means of said analysis method, to provide sample data; and in that the application of the calibration model involves linking of the sample data with the relation between the substances in order to predict the actual value for said product property.

13. A method according to claim 12, wherein the sample data is transferred into latent variables before being linked with the target value, and in that the reference sample data is transferred into latent variables before being linked with said known values.

14. A method according to claim 12, wherein the analysis method is a spectrometric method.

15. A method according to claim 14, wherein the sample data and the references sample data is processed to reduce noise and is adjusted for drift and diffuse light scatter.

16. A method according to claim 15, wherein the produced cellulose fiber-containing product is a particle board comprising one core layer and two surface layers; the cellulose fiber-containing raw material comprises sawdust, shavings, chips, or shavings from round wood, or a combination thereof; the product property is internal bond strength, thickness swelling, perforator value, or formaldehyde release; the substances are glues obtained by mixing formaldehyde, urea, and optionally any other suitable component; and the glues differ from each other with regard to the proportions between formaldehyde and urea, whereby a first glue holds a higher proportion between formaldehyde and urea than a second glue.

17. A method according to claim 14, wherein the spectrometric method is an absorption, reflectance, emission or transmission spectrometric method.

18. A method according to claim 14, wherein the spectrometric method is a NIR spectrometric method.

* * * * *